US006455478B1

(12) United States Patent
Bitton

(10) Patent No.: US 6,455,478 B1
(45) Date of Patent: Sep. 24, 2002

(54) DECORATIVE SOAP WITH EMBEDDED DISSOLVABLE IMAGE LAYER AND FURTHER COMPRISING TOY OR FIGURINE

(76) Inventor: Mary Kay Bitton, 467 Burano Ct., Oakpark, CA (US) 91377

( * ) Notice: Subject to any disclaimer, the term of this patent is extended or adjusted under 35 U.S.C. 154(b) by 0 days.

(21) Appl. No.: 09/691,529

(22) Filed: Oct. 18, 2000

Related U.S. Application Data

(63) Continuation of application No. 09/097,600, filed on Jun. 15, 1998, now Pat. No. 6,136,764.

(51) Int. Cl.[7] .................................................. A61K 7/50

(52) U.S. Cl. ....................... 510/143; 510/144; 510/147; 510/152; 510/483

(58) Field of Search ................................. 510/147, 143, 510/144, 440, 483, 152

(56) References Cited

U.S. PATENT DOCUMENTS

| | | | |
|---|---|---|---|
| 1,764,009 A | 6/1930 | Embree | |
| 1,827,549 A | 10/1931 | Villain | |
| 5,183,429 A | 2/1993 | Bitton | 446/73 |
| 5,869,437 A | 2/1999 | Wolfersberger | 510/147 |

*Primary Examiner*—Necholus Ogden
(74) *Attorney, Agent, or Firm*—K. David Crockett, Esq.; Crockett & Crockett

(57) ABSTRACT

A soap assembly comprising a transparent soap, an embedded toy, figurine or the like, and an embedded image layer. The soap assembly could also comprise a transparent soap with an embedded dissolvable image layer.

16 Claims, 1 Drawing Sheet

DECORATIVE SOAP WITH EMBEDDED DISSOLVABLE IMAGE LAYER AND FURTHER COMPRISING TOY OR FIGURINE

RELATED PATENTS

This is a continuation of U.S. application Ser. No. 09/097,600 filed Jun. 15, 1998 U.S. Pat. No. 6,136,764.

FIELD OF THE INVENTION

The present invention relates to soaps, especially transparent soaps, combined with an embedded image layer and/or figurine.

BACKGROUND OF THE INVENTION

Soaps are made with various ornamental features. Some soaps appeal to children and are shaped like characters or have characters embedded within. These soaps appeal to children and encourage them to bath longer. Other soaps appeal to adults who purchase them to adorn bath areas and the like. Still other soaps contain advertisements which of course appeal to the advertisers.

Bitton, Children's Toy and Bath Soap Assembly, U.S. Pat. No. 5,183,429, Feb. 2, 1993, describes a transparent soap with embedded toy or figurine. Villain, Manufacture of Transparent Soap Tablets containing Advertisements, U.S. Pat. No. 1,827,549, Oct. 13, 1931, describes a transparent soap containing embedded at the middle thereof a piece of paper, metal, cardboard or the like bearing an advertisement.

SUMMARY

The decorative soaps described below comprise a transparent soap, an embedded toy, figurine or the like, and an embedded image layer, resulting in a special three dimensional effect. The image layer can be dissolvable or not dissolvable in water. The decorative soaps encourage children to bath longer and also provide a useful decoration for adults who wish to adorn their bathrooms or kitchens with the soaps.

A further embodiment of the invention comprises a transparent soap with an embedded dissolvable image layer. The image layer can be a dissolvable decal. The dissolvability of the image layer is especially important when small children use the soap since once the decal dissolves, there is no residual sharp edges of the decal to cut children or long lasting remnant to create a choking hazard for children curious enough to place the remaining decal in their mouth. The elimination of the residual decal also prevents plumbing problems when the decal is washed down the drain once it peels from the soap.

DETAILED DESCRIPTION OF THE INVENTION

Figure 1:
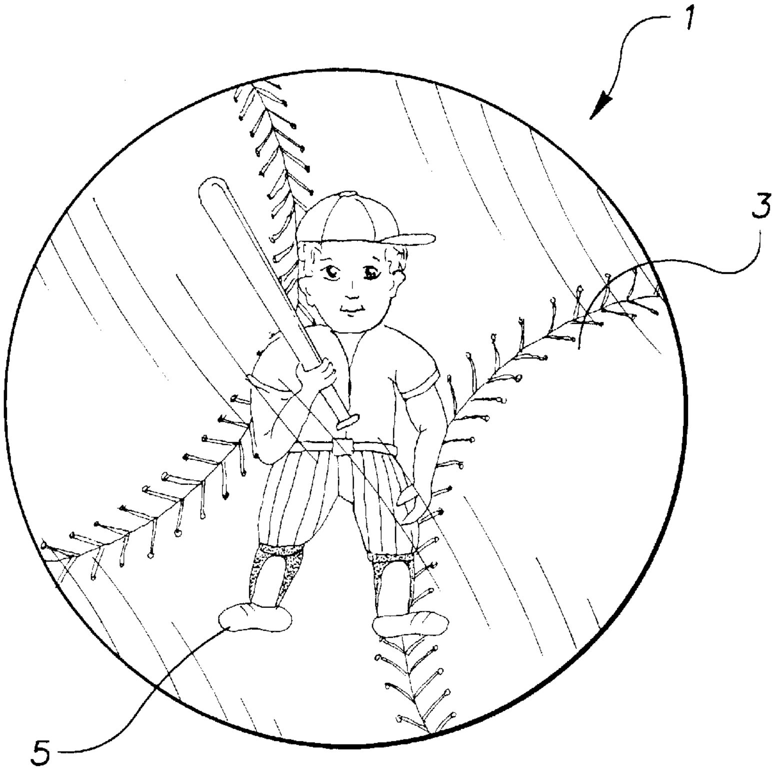
FIG. 1 is a front view of a soap with an embedded ornamental figure in the forefront and an embedded image layer in the background.
Figure 2:
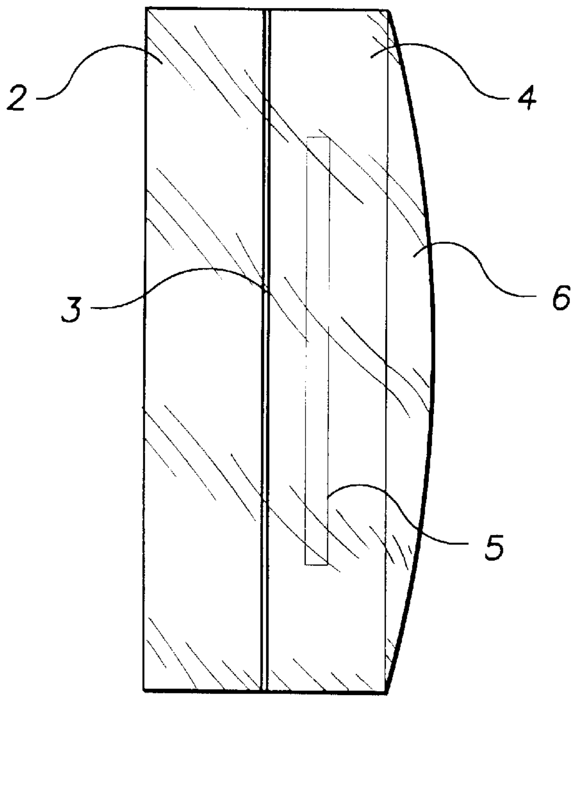
FIG. 2 is a side view of a soap with an embedded ornamental figure and image layer.

FIG. 1 shows a front view of a soap assembly with an embedded ornamental figure in the forefront and an embedded image layer in the background. FIG. 2 shows a side view of the soap assembly. The soap assembly 1 is manufactured such that a first layer of soap 2 is poured into a mold (not shown), the image layer 3 is laid on top of the first layer of soap 2, a second layer of soap 4 is poured into the mold, a figurine 5 is placed on top of the second layer of soap 4, and finally a top layer of soap 6 is poured over the soap, image layer and figurine combination. The soap assembly can also be manufactured by other processes, such as extrusion. The soap assembly can take the form of any shape, such as a bar or a ball.

The soap chosen should be transparent such that the image layer and figurine can be seen from the outside of the soap assembly. Such transparent soaps include but are not limited to glycerin soap. The first layer of soap, which comprises the bottom of the soap assembly, could be an opaque soap that would provide an ornamental background to the image layer and embedded figurine, yet would not hide or cover up the image layer and embedded figurine when viewed from the top.

The image layer 3 could be a dissolvable or non-dissolvable decal, plate, disc form or the like. If non-dissolvable, the decal, plate, disc form or the like is made of paper, metal, cardboard or the like. If dissolvable, the decal, plate, disc form or the like is made of a class of materials that dissolves, reabsorbs or is absorbable, soluble or friable in water. Examples of these materials include absorbable plastics, hydrogels, compressed sugars, compressed salts, polymers and oligomers, gelatin, pectin, and corn starch. Absorbable plastics include Polylactic Acid (PLA) and Polyglycolic Acid (PGA). These plastics can take days to dissolve in water or can be formulated with varying rates of dissolution. A specific formula can be chosen to control the reabsorption rate, and should preferably but not necessarily dissolve at the same rate as the soap. Hydrogels readily absorb or reabsorb in water such that when exposed to water, they will swell and become readily friable. Essentially, hydrogels swell so much that they disintegrate in the water. Sugars or polysaccharides, like sucrose, mannitol, or sorbitol, dissolve once the water hits them, more so than a PGA or PLA. Sugars also have anti-bacterial properties such that they will not mold in the water. Salts, such as sodium chloride, potassium chloride and sodium carbonate, also dissolve when exposed to water. Polymers and oligomers, such as dextrans, dextranes and dextrins, polyethylene glycol (PEG), polyethylene oxide, polypropyline oxide, polyvinylpyrrolidine, polyvinyl acetate and polyvinyl alcohol also dissolve in water and may be used as the material of the image layer.

Manufacture of the image layer in decal, plate or disc form will facilitate assembly of the combination. Most of the materials mentioned above can be formulated in relatively solid form (e.g. solid enough to be handled in manufacturing). In this manner the image layer may be made, decorated with paints or other colorants, and dropped into the soap mold during manufacture. Preferably, the dissolvable decal is made in a composition which may be releasably mounted on a substrate such as paper, plastic, or metal from which it may be removed for placement into the soap assembly.

A dissolvable image layer could also be a colored soap, such that you would be embedding a soap within a soap. This combination would provide the desired decorative effect yet still dissolve in water. A colored liquid could also be used that would provide the desired decorative effect yet still dissipate in water. Such colored liquids could include colored soaps, oils, glycerin or the like. The liquid should be chosen such that it would not eat away at the surrounding soap.

The figurine 5 chosen may be made in any form, representing any character, animal or thing. As shown in FIG. 1, the ornamental figurine is a baseball player and the image layer 3 a baseball. Similarly, the figurine could be a flower and the image layer a leaf or other decorative design. The figurine can be fabricated in any suitable manner, and could also be soluble like the image layer, such as if it were made of soap.

The image layer need not be in the background as shown in FIG. 1, but could also appear in the forefront and/or background. For example, the figurine could be a fish and the image layer could be aquatic plants shown in the foreground and/or background. Furthermore, the figurine could appear floating in the image layer where, for example, the image layer is a liquid. For example, a fish or mermaid could appear floating in a liquid image layer within the soap. Multiple figurines and multiple image layers can be embedded within the soap.

In another embodiment, the figurine can be eliminated, leaving a dissolvable image layer only. The dissolvable image layer can comprise a dissolvable decal, plate, disc form, colored soap, colored liquid or the like, as described above, embedded within the transparent soap.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A soap assembly comprising a transparent soap, an embedded toy, and an embedded image layer.

2. The soap assembly of claim 1 wherein the image layer is dissolvable.

3. The soap assembly of claim 2 wherein the image layer comprises a solid material which is soluble in water.

4. The soap assembly of claim 2 wherein the image layer further comprises a solid material which is soluble in water at a rate the same as the surrounding layer of soap.

5. A soap assembly comprising a transparent soap, an embedded figurine, and an embedded image layer.

6. The soap assembly of claim 5 wherein the image layer is dissolvable.

7. The soap assembly of claim 6 wherein the image layer comprises a solid material which is soluble in water.

8. The soap assembly of claim 6 wherein the image layer further comprises a solid material which is soluble in water at a rate the same as the surrounding layer of soap.

9. A soap assembly comprising a first layer of soap, a second layer of soap, an image layer, a figurine, and a third layer of soap, the second layer of soap and the third layer of soap being transparent.

10. A soap assembly comprising a first layer of soap, a second layer of soap, an image layer, a figurine, and a third layer of soap, the second layer of soap and the third layer of soap being transparent, the image layer being dissolvable.

11. The soap assembly of claim 10 wherein the image layer further comprises a solid material which is soluble in water.

12. The soap assembly of claim 10 wherein the image layer further comprises a solid material which is soluble in water at a rate approximately the same as the surrounding layer of soap.

13. A soap assembly comprising a first layer of soap, a second layer of soap, an image layer, a toy, and a third layer of soap, the second layer of soap and the third layer of soap being transparent.

14. A soap assembly comprising a first layer of soap, a second layer of soap, an image layer, a toy, and a third layer of soap, the second layer of soap and the third layer of soap being transparent, the image layer being dissolvable.

15. The soap assembly of claim 14 wherein the image layer further comprises a solid material which is soluble in water.

16. The soap assembly of claim 14 wherein the image layer further comprises a solid material which is soluble in water at a rate approximately the same as the surrounding layer of soap.

* * * * *